United States Patent
Rommelaere et al.

(10) Patent No.: US 7,267,825 B1
(45) Date of Patent: Sep. 11, 2007

(54) PARVOVIRUS VECTORS AND THEIR USE

(75) Inventors: Jean Rommelaere, Heidelberg (DE); Peter Tattersall, Guilford, CT (US)

(73) Assignees: Deutsches Krebsforschungszentrum Stiftung des offentlichen Rechts, Heidelberg (DE); Yale University, New Haven, CT (US)

( * ) Notice: Subject to any disclaimer, the term of this patent is extended or adjusted under 35 U.S.C. 154(b) by 0 days.

(21) Appl. No.: 09/807,579

(22) PCT Filed: Oct. 14, 1999

(86) PCT No.: PCT/EP99/07755

§ 371 (c)(1), (2), (4) Date: Nov. 28, 2001

(87) PCT Pub. No.: WO00/22151

PCT Pub. Date: Apr. 20, 2000

(30) Foreign Application Priority Data

Oct. 14, 1998  (EP) ................................ 98119409

(51) Int. Cl.
A61K 29/23 (2006.01)
C12N 7/00 (2006.01)
C12N 15/00 (2006.01)

(52) U.S. Cl. ............................... 424/233.1; 435/235.1; 435/320.1

(58) Field of Classification Search ............. 435/320.1, 435/235.1, 456, 69.1; 514/44; 424/93.2, 424/202.1
See application file for complete search history.

(56) References Cited

U.S. PATENT DOCUMENTS

| 5,302,517 A | | 4/1994 | Rhode | |
|---|---|---|---|---|
| 5,436,146 A | * | 7/1995 | Shenk et al. | 435/235.1 |
| 5,585,254 A | * | 12/1996 | Maxwell et al. | 435/69.1 |
| 5,693,531 A | * | 12/1997 | Chiorini et al. | 435/325 |
| 5,817,911 A | * | 10/1998 | Williams et al. | 800/2 |
| 5,952,221 A | * | 9/1999 | Kurtzman et al. | 435/320.1 |
| 6,221,646 B1 | * | 4/2001 | Dwarki et al. | 435/235.1 |

FOREIGN PATENT DOCUMENTS

WO  WO94 13823  6/1994

OTHER PUBLICATIONS

Cotmore et al. EMBO Journal 13:4145-4152, 1994.*
Ward et al. Virology 209:692-5, 1995 (abstract only cited).*
Christensen et al. Journal of Virology 75:7009-7017, 2001 (not prior art).*
Kaiser. Science 299:495, 2003 (not prior art).*
Samulski et al. Journal of Virology 61:3096-3101, 1987.*
Srivastava et al. PNAS 86:8076-8082, 1989.*
Tam et al. Virology 193, 812-824, 1993.*
Berns, K.I. Parvoviridae: the viruses and their replication. In Fields Virology, Third Edition, Ed. B.N. Fileds et al. Lipincott-Raven Publishers, Philadelphia PA, 1996, pp. 2173-2197.*
Cotmore & Tattersall, "An Asymmetric nucleotide in the parvoviral 3' hairpin directs segregation of a single active origin," *EMBO Journal*, 13(17):4145-4152 (1994) XP002096870.
Dupont, et al., "Use of an automomous parvovirus vector for selective transfer of a foreign gene into transformed human cells of different tissue origins and its expression therein," *Journal of Virology*, 68(3):1397-1406 (1994).
Maxwell, et al., "Autonomous parvovirus transduction of a gene under control of tissue-specific or inducible promoters", *Gene Therapy*, 3(1) 28-36 (1996) XP000651804 figure 1.
Tam & Astell, "Multiple cellular factors bind to cis-regulatory elements found inboard of the 5' palindrome of Minute Virus of Mice," *Journal of Virology*, 68(5): 2480-2848.

* cited by examiner

*Primary Examiner*—Bruce R. Campell
*Assistant Examiner*—M. Franco Salvoza
(74) *Attorney, Agent, or Firm*—Howrey LLP; Viola T. Kung

(57) ABSTRACT

This invention relates to a parvovirus vector having a parvovirus DNA excisable from the vector DNA in a parvovirus-permissive cell, the parvovirus DNA having a left terminus which comprises a parvovirus minimal origin of replication, and a system comprising the parvovirus vector. Furthermore, this invention concerns a method of producing the parvovirus vector, parvoviral particles as well as their use.

8 Claims, No Drawings

SEQUENCE LISTING

<160> NUMBER OF SEQ ID NOS: 4

<210> SEQ ID NO 1
<211> LENGTH: 26
<212> TYPE: DNA
<213> ORGANISM: Parvoviridae
<220> FEATURE:
<223> OTHER INFORMATION: Artificial Sequence

<400> SEQUENCE: 1
ctaagcttag catgaaagtc tctgcc                                      26

<210> SEQ ID NO 2
<211> LENGTH: 25
<212> TYPE: DNA
<213> ORGANISM: Parvoviridae
<220> FEATURE:
<223> OTHER INFORMATION: Artificial Sequence

<400> SEQUENCE: 2
gcgttaacta atagttacaa aatat                                       25

<210> SEQ ID NO 3
<211> LENGTH: 25
<212> TYPE: DNA
<213> ORGANISM: Parvoviridae
<220> FEATURE:
<223> OTHER INFORMATION: Artificial Sequence

<400> SEQUENCE: 3
gcgttaactt caagtcttcg gagtt                                       25

<210> SEQ ID NO 4
<211> LENGTH: 62
<212> TYPE: DNA
<213> ORGANISM: Parvoviridae
<220> FEATURE:
<223> OTHER INFORMATION: Artificial Sequence

<400> SEQUENCE: 4
cgcctagtac tcgagctctt cgaagcggcc gcggatccga tcgcctaggc ccgggtatcg     60
at                                                                   62

PARVOVIRUS VECTORS AND THEIR USE

This application is a National Stage of International Application PCT/EP99/07755, filed Oct. 14, 1999; which claims the priority of EP 98119409.5, filed Oct. 14, 1998.

The present invention relates to parvovirus vectors and systems containing the same. Furthermore, this invention concerns a method of producing the parvovirus vectors and their use.

Parvovirus designates a genus of the virus family Parvoviridae. The parvovirus genus comprises a number of small, icosaedric viruses that can replicate in the absence of a helper virus. Parvovirus contains a single-stranded DNA having a size of about 5.000 bp. At the 3' and 5' ends of the DNA there is one palindromic sequence each. The DNA codes for two capsid proteins, VP1 and VP2, as well as for two regulatory non-structure proteins, NS-1 and NS-2. The ex-pression of the latter proteins is controlled by a promoter, P4, while a promoter, P38, which is transactivated by NS-1, is responsible for the expression of the capsid proteins.

Parvoviruses are usually well-tolerated by populations of their natural host, in which they persist without apparent pathological signs. This is due to both the protection of foetuses and neonates by maternal immunity, and the striking restriction of parvovirus replication to a narrow range of target proliferating tissues in adult animals. This host tolerance concerns especially rodent parvoviruses, for example the minute virus of mice (MVM) and H-1 virus in their respective natural hosts, namely mice and rats. In addition, humans can be infected with the latter viruses, without any evidence of associated deleterious effects from existing epidemiological studies and clinical trials. On the other side, it is known that certain parvoviruses, and especially rodent parvoviruses, are both oncotropic, i.e. accumulate preferentially in neoplastic versus normal tissues, and oncosuppressive, i.e. have a tumorsuppressive effect towards tumor cells, in various animal models. At least part of the oncosuppressive effect is thought to be due to a direct oncolytic action mediated by the parvoviral NS1 product. This oncosuppressive effect was also demonstrated against human tumor cells transplanted in recipient animals.

This could be utilized for treating tumors. For this purpose, it is, however, desirable to modify parvoviruses in well-calculated fashion, i.e. give them new properties, e.g. to express therapeutic genes, and provide a great quantity thereof. The former appears to be possible by a parvovirus vector in which parvovirus DNA converted into a double strand is ligated with a vector DNA and the parvovirus DNA region coding for the capsid proteins is replaced by exogeneous DNA. Following the transfection of parvovirus-permissive cells, such a parvovirus vector is subjected to the excision of the parvovirus DNA and its amplification and packaging, respectively, into parvoviruses (cf. Russell, S. J. et al., Journal of Virology, 1992, 2821-2828). However, the yield of parvovirus DNA which is amplified and packed, respectively, is unsatisfactory.

Therefore, it is the object of the present invention to provide a composition by which a great quantity of packed, optionally modified, parvovirus DNA can be produced.

According to the invention this is achieved by the subject matters defined in the claims.

Thus, the subject matter of the present invention relates to a parvovirus vector having a parvovirus DNA which can be excised from the vector DNA in a parvovirus-permissive cell, the parvovirus DNA having a left terminus which comprises a minimal parvovirus origin of replication.

The present invention is based on the applicant's finding that in parvovirus-permissive cells a parvovirus present in a parvovirus vector can be excised therefrom and be replicated when its left terminus comprises a minimal parvovirus origin of replication.

The expression "parvovirus-permissive cell" comprises any cells in which a parvovirus genome can be amplified and packed into infectious viral particles. Examples of such cells are established cell lines of mice, e.g. A9 cells, of human origin, e.g. NB-E-, NB324K, 293 T cells, and of monkey cells, e.g. COS cells.

The expression "left terminus" refers to the 3' end of a parvovirus DNA available as a double strand. As mentioned above, a parvovirus DNA is usually single-stranded. However, such a DNA can be converted into a double strand by common methods. In this form it is then ligated directly or indirectly, e.g. via a linker, with a conventional vector DNA. According to the invention, the left terminus of the parvovirus DNA includes a minimal parvovirus origin of replication. For the definition of a minimal parvovirus origin of replication, reference is made to Cotmore and Tattersall, EMBO J. 13, 1994, 4145. It comprises the consensus sequence of an NS-1 nicking site. The consensus sequence is preferably CTWWTCA, W representing any nucleotide. For the provision of a minimal parvovirus origin of replication at the left terminus of the parvovirus DNA it is favorable to extend the left terminus by an inverted repeat of the unique sequence located immediately downstream from the 3' terminal palindrome of the parvovirus DNA. A person skilled in the art is familiar with processes necessary for this purpose. Reference is made to Maniatis et al., Molecular Cloning, A Laboratory Manual, Cold Spring Harbor Laboratory, 1982, by way of supplement.

As far as the "right terminus", i.e. the 5' end, of the parvovirus DNA available as a double strand is concerned, it may be the naturally occurring 5' terminus of a parvovirus DNA. It may be favorable for the 5' terminus to have internal replication sequences (IRS). They are found e.g. in the RsalA (4431-4579) and RsalB (4579-4662) fragments of the DNA of the parvovirus MVMp (cf. Tam and Astell, Virology 193, 1993, 812-824, and J. Virol. 68, 1994, 2840-2848).

In a preferred embodiment, the parvovirus DNA originates from a mammalian parvovirus, particularly a rodent parvovirus, very especially from MVM or H-1. Both rodent parvoviruses are described in the literature (cf. Astell et al.; J. Virol. 57, 1986, 656-669; Rhode and Paradiso, J. Virol. 45, 1983, 173-184; Faisst et al., J. Virol. 69, 1995, 4538-4543). It may be favorable for the parvovirus DNA to comprise a combination of DNA sequences of various parvoviruses, e.g. of mammalian parvoviruses, especially rodent parvoviruses, very especially MVM, H-1 KRV and/or LuIII. It may be particularly advantageous for the parvovirus DNA to originate from H-1 and for its left terminus to comprise a minimal parvovirus origin of replication of MVM.

According to the invention the parvovirus DNA may include an exogeneous DNA. This DNA may be inserted such that it can be expressed. For this purpose, it is favorable for it to be under the control of the parvovirus promoter P38, i.e. it partially or fully replaces the parvovirus DNA region coding for the capsid proteins. An exogeneous DNA is understood to mean any DNA. This may be e.g. an expression element such as a promoter or an enhancer, or a DNA coding for a diagnostic or therapeutic polypeptide. The latter polypeptide is particularly a cytokine, such as a lymphokine, an interleukin or a "colony stimulating factor", a chemotactic polypeptide, such as a polypeptide suitable for attracting monocytes, e.g. MCP-1, or a toxin.

According to the invention the parvovirus DNA may also include deletions of specific parts, e.g. regulatory elements, such as promoters, promoter elements, or genes coding for non-structural proteins. Instead of these deletions an exogenous DNA may be inserted.

Parvovirus vectors of choice fulfilling above conditions are exemplified below with pdBMVp, pMVM+, phH1, phH1Δ800, phH1Δ800MCP-1, phH1Δ800MCP1Δ3' and phH1Δ800hIL2 (cf. examples 1-3). These parvovirus vectors have been deposited at DSMZ (Deutsche Sammlung für Mikroorganismen und Zellkulturen) on Jul. 9, 1998 under the following DSM numbers: pdBMVp (DSM 12300), pMVM+ (DSM 12301), phH1Δ800 MCP-I (DSM 12302), phH1Δ800hL2 (DSM 12303), phH1Δ800MCP-1Δ3' (DSM 12304), phH1Δ800 (DSM 12305), phH1 (DSM 12306).

According to the invention the parvoviral genome produced from a parvovirus vector may be packaged in the form of a parvoviral particle. Such a particle is designated to as parvovirus particle and obtainable by common methods. If the parvovirus vector harbors no substitution in essential parvovirus coding and regulatory sequences, it will be an obvious choice to transfect the parvovirus vector only in cells which are parvovirus permissive. Examples of such cells are SV 40-transformed monkey kidney cells, such as COS, or SV40-transformed human kidney cells, such as NB-E, NB324K and 293T, e.g. 293T/17 and A9 mouse cells. Parvovirus vector and parvoviral particles may then be isolated from the cells.

If the parvovirus vector lacks part or all of the parvovirus DNA region coding for the parvovirus capsid proteins, it will be necessary to transfect the parvovirus vector in parvovirus-permissive cells which simultaneously express the capsid proteins of a parvovirus when parvoviral particles have to be produced. The cells may be the above cells which are transfected with a helper plasmid that permits the expression of the capsid proteins of a parvovirus. The VP proteins may also be provided by capsid genes stably integrated in the cellular genome and constitutively or inducibly expressed.

As far as the sequence coding for the structural proteins (VP) are concerned, it was discovered that certain viral sequences located in the 3' part of the genes coding for the VP proteins should be maintained in the parvovirus vector in order to obtain high titers of parvoviral particles. These sequences are not or only barely affected by deletions in the VP coding region that do not exceed approximately 800 nt starting from the ATG corresponding to the translation initiation site of the viral VP2 protein. According to the invention these sequences should be maintained if high titers of parvoviral particles have to be produced.

It may be favorable for the helper plasmid mentioned above to contain an SV40 or polyoma virus origin of replication and for the cells to express an SV40 or polyoma large T antigen. Examples of such helper plasmids are p[BK]CMV-VP and p[BK]P38-VP that are based on pBK-CMV (Strategene) and encode H-1 capsid proteins. The helper plasmids pCMVVP(MVM) and pP38VP(MVM) are based on the vector pcDNAI/Amp (Invitrogen Corporation) and can provide MVMp capsid proteins for packaging. In these constructs, the parvovirus capsid protein-coding sequences are under the transcriptional control of the human cytomegaloviurs (CMV) immediate early promotor (p[BK] CMV-VP, pCMVVP(MVM)) or the P38 parvovirus promotor (p[BK]P38-VP, pP38VP(MVM)). COS and 293 T cells can be mentioned as examples of cells which express an SV40 large T antigen. The transfection of cells expressing an SV40 large T antigen with a helper plasmid containing an SV40 origin of replication usually results in the transient expression of parvovirus capsid proteins at an extremely high level.

Furthermore, a stable expression of parvovirus capsid proteins may be advantageous. Suitable for this purpose are also the above cells, particularly 293 T cells, which are stably transfected with a helper plasmid, such as a derivative of the above-mentioned helper plasmids. It may be appropriate for the cell to have stably inserted VP coding genes under control of an inducible promotor (in particular the parvoviral P38 promotor) or a strong constitutive promotor (in particular the human or mouse CMV immediate early promotor). Above cells engineered so as to sustain a stable expression of parvovirus capsid proteins also represent a subject matter of the present invention. A person skilled in the art is familiar with transfection methods by which the transient or stable ex-pression of parvovirus capsid proteins is obtained. Cells which permit a stable expression of the capsid proteins of a parvovirus also represent a subject matter of the present invention.

Another subject matter of the present invention relates to a system comprising an above parvovirus vector and a cell expressing capsid proteins of parvovirus. It is favorable for the expression of the capsid proteins to be controlled by a helper plasmid containing an SV 40 origin of replication and for the cell to express an SV40 large T antigen. It may also be advantageous for the cell to stably express the capsid proteins of parvovirus, it being preferred when the DNA coding for the capsid proteins is controlled by the P38 parvovirus promoter.

Parvovirus vectors according to the invention distinguish themselves in that they permit higher levels of amplification of the parvovirus genomes that are excised from the parvovirus vectors. Moreover, the above-mentioned packaging cell lines (e.g. monkey COS, 293T) are highly susceptible to transfection by the convenient and cost-sparing Calcium-phosphate coprecipitation techniques or DEAE-DEXTRAN and allow the use of shuttle helper plasmids of the type discussed above. The combination of the described changes in parvovirus vector and packaging systems greatly improves the yields of parvovirus vector (parvovirus DNA insert) production giving up to 1000 times higher titers of infectious parvoviral particles as compared with the conventional parvovirus vectors packaging system, in particularly those described in Russell, S. J. et al., above. This represents a great advantage, particularly as regards time and costs. Parvovirus vector and parvoviral particles produced according to the invention are suitable for gene therapy in the best possible way. Especially a gene therapy is indicated in the case of tumor or viral diseases because of the possibility of expressing the cytotoxic viral protein NS-1 together with a therapeutic polypeptide, particularly cytokines.

The below examples explain the invention.

EXAMPLE 1

Construction of the Parvoviral Vectors pdBMVp, pMVM+ and phH1 and the Derivative Empty Parvovirus Vector phH1Δ800 According to the Invention Construction of pdBMVp: The vector pdBNco was constructed by putting NcoI linkers into the SmaI site of pUC19 and then ligating the NcoI dimer bridge (dB) fragment from pLEB711 [Cotmore, S. F. and Tattersall, P. (1992). Journal of Virology 66; 420-431] into the resulting SmaI site. pdBNco was then linearized with BamHI (in the pUC polylinker) and then partially digested with PmeI. The ends of these partials were filled in and ligated together, allowing the isolation of pdB-BP-drop, which is pdBNco deleted for the sequence between the BamHI site in the polylinker and the PmeI site in the insert nearest to BamHI. This procedure destroyed these BamHI and the PmeI sites, leaving the remaining PmeI in the insert unique. pdB-BP-drop was then digested with SapI (in the plasmid) and XbaI (in the polylinker), filled in, and ligated back together to form pdB-SX-drop, just to remove a non-essential part of the plasmid, and to render several sites within the final construct unique. To obtain the final construct, the PmeI to AatII fragment of pdB-SX-drop was replaced with the PmeI to AatII fragment of the second generation infectious clone PMVM [Gardiner, E. M. and Tattersall, P.(1988) Journal of Virology 62: 1713-1722]. The resulting third generation plasmid is the "dimer bridge" super-infectious clone of MVMp called pdBMVp.

pMVM+ is a spontaneous deletion mutation of pdBMVp missing the MVMp sequences from 4985-5003.

pH1 (infectious clone) consists of the SalI-NdeI fragement of pSR19 [Faisst et al., J. Virol. 69, 4538-4543 (1995)] containing nt 11 to nt 5110 of H-1 (EMBL GenBank#X01457) into the NdeI and SalI sites of pUC19 from which the HindIII site had been destroyed. phH1 was constructed by replacing the 1386 bp HaeII fragment of pH1 by the corresponding fragment of MVM+ containing the dimer bridge, P4 promotor and 995 nt of MVM NS1/NS2 coding region.

Thus the parvovirus DNAs carried by pdBMVp, pMVM+ and phH1 contain a MVM-minimal origin of replcation at the left (3') terminus of the viral genome and are able to provide high amounts of infectious virus upon transfection of monkey COS or 293 T cells as compared with convential parental vectors (pMVM and pSR19) and those described in Russell et al. (1992) which are deprived of a full minimal origin of DNA replication (for instance pMM984). pdB-MVp, pMVM+ and phH1 infectious clones are the starting material for the construction of parvovirus DNA containing or not foreign DNA.

For the convenient insertion of transgenes under control of the parvovirus H-1 P38 promoter, a modified parvovirus DNA was constructed from the DNA phH1, whereby the VP2 translation initiation signal (ATG) and approximately 800 nt from the downstream VP sequence were eliminated and replaced by an ochre termination signal (TAA) in frame with VP1, followed by a multiple sequence (CGC CTA GTA CTC GAG CTC TTC GAA GCG GCC GCG GAT CCG ATC GCC TAG GCC CGG GTA TCG AT, SEQ ID NO:1). More precisely, starting from position nt 2791 of phH1 [numbering according to EMBL/GenBank#X01457, Rhode and Paradiso, (1983). Journal of Virology 45, 173-184], 806 nucleotides were replaced by the above described termination signal and multiple cloning site. This created the empty parvovirus vector phH1Δ800 according to the invention.

EXAMPLE 2

Construction of Parvovirus Vectors phH1Δ800MCP-1 and phH1Δ800MCP-1A3' According to the Invention The human JE (MCP-1) cDNA [Rollings et al., Mol. Cell. Biol. 4687-4695 (1989)] was obtained from the American Type Culture Collection (ATCC, nr. 61365). The full length cDNA was isolated by PCR using a forward primer containing a HindIII site (CTAAGCTTAGCAT-GAAAGTCTCTGCO, SEQ ID NO:2) and a reverse primer with an incorporated HpaI site (GCGTTAACTAATAGTTA-CAAAATAT, SEQ ID NO:3). After digestion with SacI and HpaI, tha 701 bp PCR fragment was cloned between the SacI and the SmaI restriction sites of phHΔ800, to create phH1Δ800MCP-1 according to the invention. The MCP-1 cDNA deprived of its 3' untranslated region (3'UTR) was amplified using the same forward primer and the reverse primer (GCGTTAACTTCAAGTCTTCGGAGTT, SEQ ID NO:4) with an incorporated HpaI site. After digestion with SacI and HpaI, the 355 bp PCR fragment was cloned between the SacI and SmaI restriction sited of phHΔ800 to generate phH1Δ800MCP-1A3'. Both vector DNAs achieve high titers of parvoviral particles when parvoviral capsid proteins are simultaneously expressed from a helper plasmid as described above.

EXAMPLE 3

Construction of the Parvovirus Vectors phH1Δ800HIL2 According to the Invention The cDNA coding for human IL2 deprived of its 3' untranslated region was excised from the plasmid M13TG5317 (Transgene, Strasbourg) by hydolysis with SalI, and inserted in the SalI site of pBluescript SK+, (EMBL/GenBank#X52325) giving phIL2. phIL2 was cut with XhoI and BamHI and the 539 bp fragment was inserted in the XhoI and BamHI hydrolysed empty parvovirus vector phH1Δ800 (see example 1), generating the human IL2 expressing parvovirus vector phHΔ800hIL2, from which parvovirus DNA and parvoviral particles can be produced.

EXAMPLE 4

Production of High-Titer Stocks of Parvoviral Particles

The genes coding fot the structural proteins of parvovirus H-1 or MVMp under control of the genuine parvoviral promotor P38 or the human CMV immediate early promoter are cloned in the shuttle vector pBK-CMV (Stratagene) or pcDNAI/Amp (Invitrogen), both containing an SV40 origin of replication, this gives rise to the helper plasmids p[BK] P38-VP and p[BK]CMV-VP, which provide H-1 capsid proteins, or pCMVVP(MVM) and pP38VP(MVM), which provide MVMp capsids. 293T cells are transfected with one of the VP-expressing helper plasmids and one of the above parvovirus vectors according to the invention. Parvoviral particles are recovered from the cells and titered by a filter hybridization technique [Russell et al., 1992]. From the parvovirus vectors described in examples 2-3, titers of up to 10⁸ replication units of parvoviral particles (described in the examples 2-3) per ml of crude extract can be obtained in this way.

The invention claimed is:

1. A parvovirus vector comprising a parvovirus DNA having a left terminus which comprises a parvovirus minimal origin of replication comprising CTWWTCA, wherein W is any nucleotide, and the parvovirus DNA is excisable from the parvovirus vector in a parvovirus-permissive cell, wherein the parvovirus DNA region coding for capsid proteins is partially or fully replaced by an exogeneous DNA coding for a chemotactic polypeptide.

2. The parvovirus vector according to claim 1, wherein the parvovirus DNA originates from a mammalian parvovirus.

3. The parvovirus vector according to claim 1, wherein the parvovirus DNA is a rodent parvovirus.

4. The parvovirus vector according to claim 3, wherein the rodent parvovirus is MVM or H-1.

5. The parvovirus vector according to claim 1, wherein the chemotactic polypeptide is MCP-1.

6. The parvovirus vector according claim 1, wherein the parvovirus vector is present as a parvoviral particle.

7. A system comprising a parvovirus vector and a cell expressing the capsid proteins of parvovirus, wherein the parvovirus vector comprising a parvovirus DNA having a left terminus which comprises a parvovirus minimal origin of replication comprising CTWWTCA, wherein W is any nucleotide, and the parvovirus DNA is excisable from the parvovirus vector in a parvovirus-permissive cell, wherein the parvovirus DNA region coding for capsid proteins is partially or fully replaced by an exogenous DNA, wherein the expression of the capsid proteins is controlled by a helper plasmid comprising an SV40 origin of replication and the cell expresses an SV40 large T antigen.

8. The system according to claim 7, wherein the DNA coding for the capsid proteins is under the control of the parvovirus promoter P38.

* * * * *